United States Patent
Krone et al.

Patent Number: 6,036,948
Date of Patent: *Mar. 14, 2000

[54] POLYASPARTAMIDE DERIVATIVES AS ADSORDENTS FOR BILE ACIDS, POLYASPARTAMIDE DERIVATIVES LOADED WITH BILE ACIDS AND PROCESS FOR THEIR PREPARATION AND THEIR USE AS PHARMACEUTICALS

[76] Inventors: Volker Krone, Zu den Eichen 25, D-6238, Hofheim am Taunus; Axel Walch, Hans-Sacjs-Strasse 5, D-6000, Frankfurt am Main; Stefan Müllner, Friedrich-Ebert-Strasse 43, D-6203, Hocheim am Main; Ernold Granzer, Falkensteiner Strasse 24, D-6233, Kelkheim, all of Germany

[ * ] Notice: This patent is subject to a terminal disclaimer.

[21] Appl. No.: 08/956,122

[22] Filed: Oct. 22, 1997

Related U.S. Application Data

[62] Division of application No. 08/164,767, Dec. 10, 1993, Pat. No. 5,714,138, which is a continuation of application No. 07/992,093, Dec. 17, 1992, abandoned.

[30] Foreign Application Priority Data

Dec. 20, 1991 [DE] Germany ............... 0 41 42 147

[51] Int. Cl.$^7$ ............ A61K 31/765; A61K 31/785; C08G 69/36
[52] U.S. Cl. .................. 424/78.12; 424/78.17; 525/420; 525/434
[58] Field of Search ............... 525/54.1, 54.11, 525/420, 434; 424/78.12, 78.17

[56] References Cited

U.S. PATENT DOCUMENTS

| | | | |
|---|---|---|---|
| 5,516,758 | 5/1996 | Stevens et al. | 514/12 |
| 5,714,138 | 2/1998 | Krone et al. | 424/78.12 |

FOREIGN PATENT DOCUMENTS

| | | |
|---|---|---|
| 2424293 | 12/1979 | France . |
| 0747901 | 4/1956 | United Kingdom . |
| 1024393 | 3/1966 | United Kingdom . |
| 1202765 | 8/1970 | United Kingdom . |

*Primary Examiner*—Jeffrey C. Mullis

[57] ABSTRACT

Polyaspartamide derivatives as adsorbents for bile acids, polyaspartamide derivatives loaded with bile acids and process for their preparation and their use as pharmaceuticals α- or β-linked polyaspartamide derivatives of the formula I

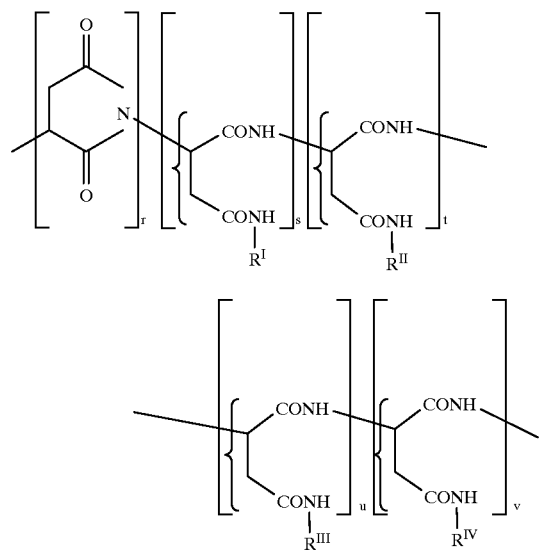

in which $R^I$, $R^{II}$, $R^{III}$, $R^{IV}$, r, s, t, u and v have the stated meanings, are described. They adsorb bile acids and can be used as pharmaceuticals.

7 Claims, No Drawings

POLYASPARTAMIDE DERIVATIVES AS ADSORDENTS FOR BILE ACIDS, POLYASPARTAMIDE DERIVATIVES LOADED WITH BILE ACIDS AND PROCESS FOR THEIR PREPARATION AND THEIR USE AS PHARMACEUTICALS

This is a division of application Ser. No. 08/164,767, filed Dec. 10, 1993, now U.S. Pat. No. 5,714,138 which in turn is a continuation of application Ser. No. 07/992,093, filed Dec. 17, 1992, abandoned.

The invention relates to water-soluble and -insoluble polyaspartamides, polyaspartamide derivatives which are loaded with bile acids, a process for their preparation and their use as pharmaceuticals.

Bile acids have an important physiological function in fat digestion, for example as cofactors of pancreatic lipases. As the end product of cholesterol metabolism, they are synthesized in the liver, stored in the gall bladder and released from this by contraction into the small intestine, where they display their physiological action.

The major part of the secreted bile acids is recovered again via the enterohepatic circulation, and returns to the liver again via the mesenterial veins of the small intestine and the portal vein system. Both active and passive transport processes play a role in reabsorption in the intestine. In the enterohepatic circulation, the bile acids occur as free acids, but also in the form of glycine and taurine conjugates.

It was known hitherto to bind bile acid to non-absorbable, insoluble, basic crosslinked polymers (ion exchange resins="resins"). The subject of treatment is regarded as encompassing all diseases in which an inhibition of bile acid reabsorption in the intestine, in particular in the small intestine, appears desirable. For example, chologenic diarrhea after ileum resection, or alternatively increased cholesterol blood levels are treated in this manner. In the case of the increased cholesterol blood level, a reduction of this level can be achieved by intervention in the enterohepatic circulation. As a result of reduction of the bile acid pool found in the enterohepatic circulation, the corresponding de novo synthesis of bile acids from cholesterol in the liver is enforced. To cover the cholesterol requirement in the liver, resort is made to the LDL cholesterol (low density lipoprotein) present in the blood circulation, the hepatic LDL receptors coming into action in increased number. The acceleration of LDL catabolism thus achieved has an effect by way of the reduction of the atherogenic cholesterol content in the blood. Until now, said polymeric, insoluble ion exchange resins represented the only possibility of affecting the enterohepatic circulation with respect to increased bile acid secretion and the reduction of the cholesterol level following therefrom.

It now appears that the pharmaceuticals which are based on crosslinked ion exchange resins have various disadvantages.

For the "resins" being used as pharmaceuticals, a very high daily dose, in particular, has to be maintained. This amounts, for example for colestyramine (contains quaternary ammonium groups) to 12–14 g, maximum dose 32 g, and for colestipol (contains secondary and tertiary amino groups) to 15–30 g.

A further disadvantage is that taste, odor and said high dosage make patient compliance difficult.

It is furthermore known that conventional "resins" exhibit side effects. These side effects are due to lack of selectivity (for example avitaminoses), which also have to be taken into account in the dosage of simultaneously administered medicaments, but also to bile acid depletion, which causes various gastrointestinal disorders (obstipation, steatorrhea) of various degrees.

For both preparations, a therapeutic importance as a result of combination with other hypolipidemic pharmaceuticals such as fibrates, HMG-COA reductase inhibitors, probucol (cf., for example, M.N. Cayen, Pharmac. Ther. 29, 187 (1985) and 8th International Symposium on Atherosclerosis, Rome, Oct. 9–13, 1988, Abstracts pp. 544, 608, 710) has been described, where the effects achieved also make possible the therapy of severe hyperlipidemias. It therefore appears significant, given the principle of action, to find suitable substances without the disadvantages of the currently used preparations. The following features of said preparations and in particular of colestipol are regarded as worthy of improvement:

1. The high daily doses which are necessary since only a relatively low binding rate obtains at neutral pH in isotonic medium, and the (partial) re-release of the adsorbed bile acids.
2. The qualitative shift in the bile acid composition of the bile with a decreasing tendency for chenodesoxycholic acid and the increasing risk of cholelithiasis associated therewith.
3. The lack of a damping effect on the cholesterol metabolism of the intestinal bacteria.
4. The excessively high binding rate of vitamins and pharmaceuticals may make it necessary to replace those substances and to check blood levels.
5. The administration form was until now to be regarded as inadequate.

It was the object of the invention to provide a possibility of binding bile acids in a concentration-dependent manner, the compounds binding the bile acids themselves not being co-absorbed and thus not passing into the enterohepatic circulation. The compounds should also have a high binding rate for bile acids at neutral pH and simultaneously ensure that these are not released again under physiological conditions and thus cannot be absorbed.

Moreover, these compounds should not or no longer to known extent have the existing disadvantages of the known "resins".

The object is solved by the provision of α- or β-linked polyaspartamide derivatives of the formula I

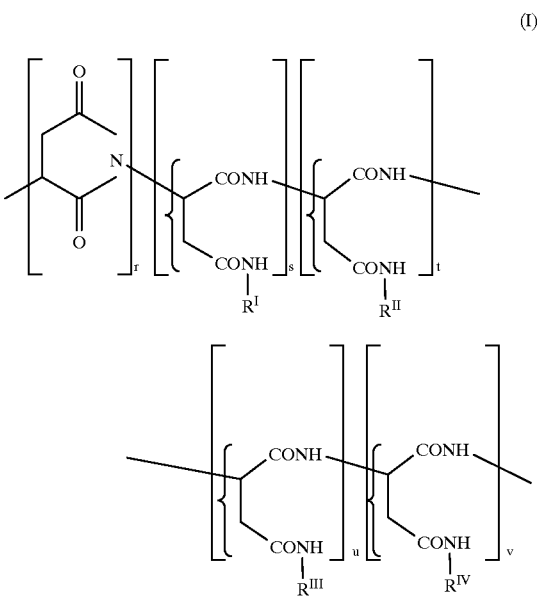

in which
$R^I$, $R^{II}$, $R^{III}$ and $R^{IV}$ are identical or different and are H, a radical of the formula II

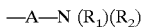   II in which
A is an alkylene, alkenylene or alkynylene radical having 2 to 15, preferably 2 to 6, carbon atoms, which is straight-chain or branched, preferably straight-chain, $R_1$ and $R_2$ independently of one another are hydrogen or $(C_1-C_{18})$-alkyl, preferably $(C_1-C_3)$-alkyl,
a radical of the formula III

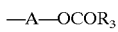   III or a radical of the formula IV

   IV in which
A has the abovementioned meaning and $R_3$ is the radical which is a natural or synthetic fatty acid bonded via its carboxyl group or a dicarboxylic acid or a dicarboxylic acid ester or amide respectively having 2–8 carbon atoms, and
r is 0 to 0.5,
s is 0.1 to 0.9,
t is 0.9 to 0.1,
u is 0 to 0.5 and
v is 0 to 0.5.

It is particularly preferred if r or u is zero or the sum of r and u is equal to zero.

$R^I$ is preferably a radical of the formula II and $R^{II}$, and $R^{III}$ are a radical of the formula III, and, if appropriate, $R^{IV}$ is a radical of the formula IV.

Particularly preferred compounds according to the invention are those in which $R^{II}$ and $R^{III}$ carry different radicals of the formula III.

The dicarboxylic acid derivatives include succinoyloxybutyl and -hexyl radicals.

Physiologically acceptable aromatic carboxylic acid radicals, such as, for example, cinnamic acid or dihydrocinnamic acid can also be employed.

Of the alcohols which represent the ester component in the dicarboxylic acid esters, the following are employed: saturated and unsaturated, linear or branched alcohols such as hexanol, octanol, decanol, dodecanol, tetradecanol, hexadecanol, octadecanol and the like. Likewise, the alcohols are also to be understood as meaning those which can carry further OH groups, such as, for example, 1,2-hexanediol, 1,2-dodecanediol or 1,2-hexadecanediol.

The compounds according to the invention in general have a molecular weight of $10^3$ to $10^6$, preferably of $10^4$ to $10^5$.

The degree of substitution of the radicals $R^I$, $R^{II}$, $R^{III}$, $R^{IV}$ to be attained, based on an aspartamide unit, is dependent on the radical employed and on the reaction conditions selected. Finally, it is set in such a manner that the pharmacological action of the compounds according to the invention to be attained is optimally achieved.

In general, the degree of substitution DS is between 0.1 and 1.0, preferably between 0.2 and 0.8 for $R^I$ and $R^{II}$. For $R^{III}$, values between 0.1 and 0.5 are preferably set.

The derivatization of the polyaspartamide with the compounds of the formulae II and III leads to lipophilization of the polymer. This lipophilization leads to the bile acids being firmly bound to the polymer adsorptively to an increased extent and in particular at a physiological pH. In this case, the binding consists of an ionic and a structural interaction between the bile acid molecule and the polyaspartamide molecule.

Bile acids are ionized or protonated at physiological pH. To that extent, there is an ionic interaction. The structural interaction is based on the fact that bile acids are spatially surrounded by the lipophilized polyaspartamide molecule. This is, therefore, a case of inclusion compounds.

Basically, it is therefore possible both to ionize the polyaspartamide derivatives (amino acid, aminoalkoxy radicals) and to lipophilize them (fatty acids, alcohols), it being possible for the adsorptive actions to be enhanced. It is likewise possible to employ bile acids as derivatization reagents for polyaspartamides, and to use the derivatives as adsorbers for bile acid.

In this case, the degree of substitution for the covalently bonded bile acids is 0.01 to 1, preferably 0.3 to 0.8.

Natural amino acids which can be mentioned are: glycine, L-alanine, L-valine, L-leucine, L-serine, L-threonine, L-lysine, L-arginine, L-asparagine, L-glutamine, L-phenylalanine, L-tyrosine, L-proline, L-tryptophan.

Preferred synthetic amino acids are enantiomer mixtures of the natural amino acids, homoamino acids, isoamino acids, γ-aminobutyric acid, a-aminobutyric acid etc.

Suitable fatty acids are saturated or unsaturated, straight-chain or branched carboxylic acids such as caproic acid, heptanoic acid, octanoic acid, decanoic acid, dodecanoic acid, tetradecanoic acid, hexadecanoic acid, octadecanoic acid, oleic acid, linoleic acid, linolenic acid, 2-methylhexanoic acid and the like.

The following alcohols, for example, are employed for lipophilization: saturated and unsaturated, linear or branched alcohols such as hexanol, octanol, decanol, dodecanol, tetradecanol, hexadecanol, octadecanol and the like. Likewise, the alcohols are also to be understood as meaning those which can carry further OH groups, such as, for example, 1,2-hexanediol, 1,2-dodecanediol or 1,2-hexadecanediol.

The following aminoalkyl radicals of the formula A—N $(R_1)(R_2)$ are used: 2-aminoethanol, 3-aminopropanol, N,N-dimethyl- or -diethyl-2-aminoethanol, N,N-dimethyl- or -diethyl-3-aminopropanol, 4-aminobutanol, 6-aminohexanol, 4-aminobutyric acid, 6-aminocaproic acid, and the like.

The following bile acids can be bound to the polyaspartamides according to the invention: cholic acid, deoxycholic acid, lithocholic acid, ursodeoxycholic acid, chenodeoxycholic acid, and their corresponding taurine and glycine conjugates.

By use of the compounds according to the invention, the described deficiencies of the "resins" intervening in the enterohepatic circulation, which are found on the market, can be completely eliminated. By inhibiting bile acid reabsorption in the small intestine with the aid of the compounds according to the invention, the bile acid concentration found in the enterohepatic circulation is reduced in a substantially more effective manner, such that a reduction of the cholesterol level in the serum takes place. Avitaminoses, when using the compounds according to the invention, are seen just as little as the effect on the absorption of other pharmaceuticals or alternatively the negative action on the intestinal flora, since the bile acid binding to the compounds according to the invention is an extremely stable.

By use of the compounds according to the invention, the otherwise customary dosage of the resins can be considerably reduced; the recommended dose is 0.5–10 g/kg/day. The known side effects (obstipation, steratorrhea) have therefore not been observed, i.e. fat digestion is not adversely affected, due to the almost natural structure of the polyaspartamides on the one hand and the known positive effect of so-called ballast substances on the digestion on the other hand.

Because of the high affinity of the compounds according to the invention for bile acids, the problem of dosage and as a result also that of compliance no longer arises, compared with the high daily dose of "resins". In addition, the compliance is improved by the fact that the polyaspartamides according to the invention are water-soluble and thus no additives such as, for example, flavor enhancers, emulsifiers, sweeteners etc. are required for formulation.

The preparation of polysuccinimide (=polyanhydroaspartic acid) is known from EP-A-0,439, 846 (corresponding to U.S. patent application No. 651,295).

The invention furthermore relates to the conjugate of the polyaspartamide derivative according to the invention and at least one bile acid, which is bonded adsorptively to the polyaspartamide derivative as a result of a structural interaction.

The invention furthermore relates to the use of the complexes according to the invention for the production of a pharmaceutical. The compounds are dissolved or suspended or mixed in pharmacologically acceptable organic solvents, such as mono- or polyhydric alcohols such as, for example, ethanol or glycerol, in triacetin, oils, such as, for example, diethylene glycol dimethyl ether, or alternatively polyethers, such as, for example, polyethylene glycol, or alternatively in the presence of other pharmacologically acceptable polymer supports, such as, for example, polyvinylpyrrolidone, or other pharmaceutically acceptable additives such as starch, cyclodextrin or polysaccharides. The compounds according to the invention can also be administered in combination with other pharmaceuticals.

The conjugates according to the invention are administered in various dosage forms, preferably orally in the form of tablets, capsules or liquids, which may include, for example, foodstuffs or fruit juices.

The polyaspartamides according to the invention can additionally be used in analytical processes for the group-selective enrichment of bile acids from biological fluids such as, for example, plasma, serum, urine, bile etc.

Determination of the adsorber capacity

For in-vitro testing of the adsorber capacity of the compounds according to the invention, the following bile acids: 15.1 mg of cholic acid, 13.8 mg of deoxycholic acid, 13.8 mg of chenodeoxycholic acid, 13.2 mg of lithocholic acid, 17.1 mg of glycocholic acid, 15.8 mg of glycodeoxycholic acid, 16.6 mg of glycochenodeoxycholic acid and 16.0 mg of glycolithocholic acid are dissolved in 700 µl of methanol, mixed with 0.92 ml of phosphate-buffered saline solution (pH 7.2) and incubated for 24 h at 37° C. in a shaking water bath together with 5 mg of the compounds according to the invention. The mixture is then poured into a dialysis tube of the Visking type and dialysed against phosphate-buffered saline solution (pH 7.2) at room temperature for 72 h. The bile acid binding is determined by analysis of the external medium, for example by the methods described in the following.

1) HPLC with fluorescence detection
   Equipment:
   HPLC unit from Kontron, comprising three pumps and mixing chamber, autosampler, UV detector and analysis unit with MT2 software. Fluorescence detector from Merck and Hitachi. Since the samples are light- and heat-sensitive, the autosampler is cooled to about 5° C.

Mobile phase:
Eluent A: ®Millipore water (in-house unit)
Eluent B: Acetonitrile/methanol 60:30
Column:
®LiChrospher 100 RP-18, 25 mm, 5 µm, Merck
Precolumn:
LiChrospher 60 RP-select B, 4 mm, 5 µm, Merck
Flow rate:
1.3 ml/min
Detection:
Excitation: 340 nm
Emission: 410 nm
Gradient:
0.00 min 66% B
7.50 min 66% B
8.00 min 76% B
12.50 min 76% B
13.00 min 83% B
25.00 min 83% B
25.50 min 91% B
40.00 min 91% B 2) Enzymatic determination of total bile acid
900 µl each of the following mixture are added to Eppendorf vessels:
   6 ml of tetrasodium diphosphate buffer 0.1 M, pH 8.9
   2 ml of AND solution (4 mg/ml water)
   20 ml Millipore water
   30 µl of the sample and 30 µl of enzyme solution are pipetted into this.
   Enzyme solution: 3-alpha-hydroxysteroid dehydrogenase 0.5 units/ml
The batches are mixed and incubated at room temperature for 2 h.
Subsequent transfer to 1 ml disposable cuvettes and measurement in a photometer at 340 nm.
Only of limited use for bile acid samples, since the green color interferes.

3) HPLC with UV detection
   Equipment:
   HPLC unit from Kontron, comprising three pumps and mixing chamber, autosampler, UV detector and analysis unit with MT2 software.
   Mobile phase:
   Eluent A: Ammonium carbamate buffer 0.019 M, adjusted with phosphoric acid to pH 4.0.
   Eluent B: Acetonitrile
   Column:
   LiChrospher 100 RP-8, 25 mm, 5 µm, Merck
   Precolumn:
   LiChrospher 60 RP-select B, 4 mm, 5 µm, Merck
   Flow rate:
   Gradient:
      0.00 min 0.8 ml/min
      20.00 min 0.8 ml/min
      23.00 min 1.3 ml/min
      51.00 min 1.3 ml/min
   Detection:
   200 nm (for preparations additionally at 254 nm)
   Gradient:
   0.00 min 32% B 8.00 min 35% B
17.00 min 38% B
20.00 min 40% B
24.00 min 40% B
30.00 min 50% B
45.00 min 60% B The following results could be obtained. They are summarized in FIG. 1. FIG. 1 shows the adsorption properties of the polyaspartamide derivatives according to the invention with respect to:

| | |
|---|---|
| C | cholic acid |
| CDC | chenodeoxycholic acid |
| DC | deoxycholic acid |
| LC | lithocholic acid. |

The compounds were prepared as follows:

EXAMPLE 1

Preparation of poly-α,β-(hydroxyethyl)-D,L-aspartamide-co-α,β-(dimethylaminoethyl)-D,L-aspartamide (40:60)

10 g (103 mmol) of polyanhydroaspartic acid ($M_{visc.}$=25,000) are dissolved in 80 ml of DMF (anhydrous), if appropriate with gentle warming. First, 2.5 g (41 mmol) of freshly distilled dimethylaminoethylamine diluted in 20 ml of DMF are added dropwise to this solution and 1 g of anhydrous 2-hydroxypyridine is added and the mixture is stirred at room temperature for one day. 8.8 g (100 mmol) of aminoethanol are then added. After stirring for a further day, the mixture is warmed to 50° C. for 2 h and the DMF is evaporated in a rotary evaporator at 40° C. The residue is dissolved in water and ultrafiltered through a 10,000 membrane. The retentate is lyophilized and the composition of the copolymer obtained is checked by NMR spectroscopy.

Yield: 9.5 g.

$^1$H NMR (300 MHz) in $D_2O/CF_3COOD$:
a) singlet at 2.79 ppm, —N(CH$_3$)$_2$
b) broad signal at 2.66 ppm, CH$_2$ (main chain)
c) broad signals at 3.14 ppm and 3.46 ppm, 4H, CH$_2$ (side chains)
d) broad signals around 4.2 ppm and 4.55 ppm, 1H, CH (main chain).

EXAMPLE 2

Preparation of poly-α,β-(hydroxyethyl)-D,L-aspartamide-co-α,β-(dimethylaminoethyl)-D,L-aspartamide (75:25)

15 g (155 mmol) of polyanhydroaspartic acid ($M_{visc.}$=19,000) are dissolved in 80 ml of DMF (anhydrous), if appropriate with gentle warming. First, 3.40 g (39 mmol) of freshly distilled dimethylaminoethylamine diluted in 20 ml of DMF are added dropwise to this solution and 1 g of anhydrous 2-hydroxypyridine is added and the mixture is stirred at room temperature for one day. 10 g (164 mmol) of aminoethanol are then added. After stirring for a further day the mixture is warmed at 50° C. for 2 h and repeatedly precipitated in anhydrous acetone.

Yield: 24 g.

EXAMPLE 3

Preparation of polyanhydroaspartic acid-co-α,β-(hydroxyethyl)-D,L-aspartamide-co-α,β-(dimethylaminoethyl)-D,L-aspartamide (15:20:65)

10 g (103 mmol) of polyanhydroaspartic acid are dissolved in 80 ml of DMF (anhydrous), if appropriate with gentle warming, and 1 g of hydroxypyridine is added. 5.9 g (67 mmol) of dimethylaminoethylamine, dissolved in 20 ml of DMF, are then added dropwise and the mixture is stirred at room temperature for one day. 1.25 g (20.6 mmol) of aminoethanol, diluted in 10 ml of DMF, are then added. Likewise after one day at room temperature, the mixture is warmed at 60° C. for 3 hours to complete reaction, and repeatedly precipitated in anhydrous acetone.

EXAMPLE 4

Preparation of polyanhydroaspartic acid-co-α,β-(palmitoyloxyethyl)-D,L-aspartamide-co-α,β-(dimethylaminoethyl)-D,L-aspartamide (15:20:65)

10 g of polyanhydroaspartic acid-co-α,β-(hydroxyethyl)-D,L-aspartamide-co-α,β-(dimethylaminoethyl)-D,L-aspartamide (15:20:65) from Example 3 are dissolved in 100 ml of anhydrous and amine-free DMF and 10 ml of palmitoyl chloride are slowly added. 10 ml of pyridine which contains a spatula tipful of DMAP are then added dropwise and the mixture is stirred overnight. To complete the reaction, the mixture is then warmed at 60° C. for 2 hours. The batch is repeatedly precipitated in anhydrous acetone and dried in vacuo.

EXAMPLE 5

Preparation of poly-α,β-(palmitoyloxyethyl)-D,L-aspartamide-co-α,β-(dimethylaminoethyl)-D,L-aspartamide (40:60)

10 g of poly-α,β-(palmitoyloxyethyl)-D,L-aspartamide-co-α,β-(dimethylaminoethyl)-D,L-aspartamide (40:60) from Example 1 are dissolved in 100 ml of anhydrous and amine-free DMF and 15 ml of palmitoyl chloride are added. 15 ml of pyridine are added dropwise and a spatula tipful of DMAP is added. The mixture is stirred overnight and warmed to 60° C. for 2 hours to complete the reaction. The initially heterogeneous reaction mixture becomes clear during the course of this. It is then precipitated in acetone, the precipitate is dried and dissolved in water with warming (turbid) and, after filtering, ultrafiltered through a 10,000 membrane and the retentate is then lyophilized.

Yield: 10.7 g.

EXAMPLE 6

Preparation of poly-α,β-(palmitoyloxyethyl)-D,L-aspartamide-co-α,β-(3-butoxycarbonyl) propionyloxyethyl)-D,L-aspartamide-co-α,β-(dimethylaminoethyl)-D,L-aspartamide (15:60:25)

5 g of poly-α,β-(hydroxyethyl)-D,L-aspartamide-co-α,β-(dimethylaminoethyl)-D,L-aspartamide (75:25) are dissolved in 60 ml of dried DMF. 1.25 g (1.4 ml) of palmitoyl chloride and 3.5 g of 3-butoxycarbonylpropanoyl chloride are weighed into a dropping funnel and made up to 10 ml with dry DMF. The solution is slowly added dropwise. 2 ml of pyridine are then dissolved in 3 ml of DMF and likewise slowly added dropwise to the reaction mixture. After 3 hours, the procedure of acid chloride and pyridine addition is repeated and the batch is stirred over the course of a further 5 days. The batch is then precipitated in diisopropyl ether, and the residue is dried and then dissolved in water. It is ultrafiltered through a 10,000 membrane and the retentate is lyophilized. The composition must be checked by NMR spectroscopy. To do this, the following signals are used:

$^1$H NMR in $D_2O$: broad triplet around 0.85 ppm, CH$_3$ of the palmitoyl and butyl groups, broad signal between 1.05 and 2 ppm, one CH$_2$ group from the butoxy branch and 13

CH$_2$ groups from the palmitoyl radical; the ratio of butoxycarbonylpropionyloxyethyl groups to palmitoyl groups can be calculated from this, singlet at 3 ppm, (CH$_3$)N—, the ratio of ester groups to amino groups follows from this.

EXAMPLE 7

Preparation of poly-α,β-(palmitoyloxyethyl)-D,L-aspartamide-co-α,β-(3-butoxycarbonyl)propionyloxyethyl)-D,L-aspartamide-co-α,β-(dimethylaminoethyl)-D,L-aspartamide-co-α,β-(hydroxyethyl)-D,L-aspartamide (15:50:25:10)

5 g of poly-α,β-(hydroxyethyl)-D,L-aspartamide-co-α,β-(dimethylaminoethyl)-D,L-aspartamide (75:25) are dissolved in 60 ml of dried DMF. 1.25 g (1.4 ml) of palmitoyl chloride and 3.5 g of 3-butoxycarbonylpropanoyl chloride are weighed into a dropping funnel and made up to 10 ml with dry DMF. The solution is slowly added dropwise. 2 ml of pyridine are then mixed with 3 ml of DMF and likewise slowly added dropwise to the reaction mixture. After stirring overnight, the batch is then precipitated in diisopropyl ether, and the residue is dried and then dissolved in water. The solution is ultrafiltered through a 10,000 membrane and the retentate is lyophilized. Analysis analogously to Example 6.

In contrast to Example 6, the reaction is substantially incomplete and gives a product containing about 10% unesterified hydroxyl groups.

EXAMPLE 8

Preparation of α,β-poly(2-dimethylaminoethyl)-co-(palmitoyloxyethyl)-D,L-aspartamide (80:20)

Preparation is carried out analogously to Example 5. Yield: 10.2 g.

EXAMPLE 9

Preparation of α,β-poly(2-dimethylaminoethyl)-co-(palmitoyloxyethyl)-D,L-aspartamide (40:60)

Preparation is carried out analogously to Example 5. Yield: 10.6 g.

EXAMPLE 10

Preparation of α,β-poly(2-dimethylaminoethyl)-co-(palmitoyloxyethyl)-D,L-aspartamide (20:80)

Preparation is carried out analogously to Example 5. Yield: 10.5 g.

We claim:
1. A conjugate comprising at least one bile acid and a compound of the formula (I):

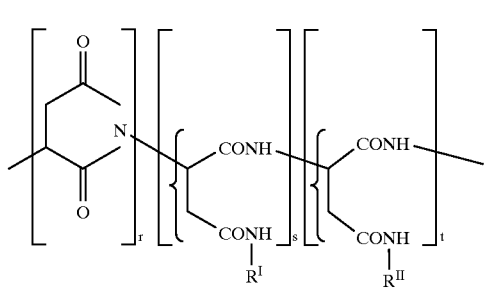
(I)

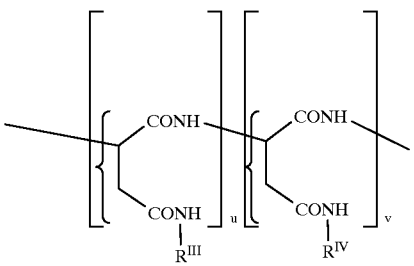
-continued in which
R$^I$ is H or a radical of the formula II

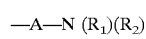
—A—N(R$_1$)(R$_2$)     II in which
A is an alkylene, alkenylene or alkynylene radical having 2 to 15, carbon atoms, which is straight-chain or branched, R$_1$ and R$_2$ independently of one another are hydrogen or (C$_1$–C$_{18}$)-alkyl, and
R$^{II}$, R$^{III}$ and R$^{IV}$ are identical or different and are H; a radical of the formula III

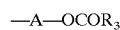
—A—OCOR$_3$     III in which
A has the above-mentioned meaning and —OCOR$_3$ is a natural or synthetic fatty acid bonded via its carboxyl group;
or a radical of the formula IV

—A—OH     IV in which
A has the abovementioned meaning,
r is 0 to 0.5,
s is 0.1 to 0.9,
t is 0.9 to 0.1,
u is 0 to 0.5 and
v is 0 to 0.5,
and in which the sum of r, s, t, u and v is one.

2. A pharmaceutical comprising a conjugate as claimed in claim 1 and an excipient.

3. A hypolipidemic composition comprising a conjugate as claimed in claim 1.

4. A composition comprising a conjugate as claimed in claim 1 and a foodstuff or a fruit juice.

5. The conjugate as claimed in claim 1, wherein A is a straight-chain alkylene, alkenylene or alkynylene radical having 2 to 15 carbon atoms.

6. The conjugate as claimed in claim 1, wherein A is an alkylene, alkenylene or alkynylene radical having 2 to 6 carbon atoms.

7. The conjugate as claimed in claim 1, wherein R$_1$ and R$_2$ independently of one another are hydrogen or (C$_1$–C$_3$)-alkyl.

* * * * *